United States Patent
Kang et al.

(10) Patent No.: US 11,192,047 B2
(45) Date of Patent: Dec. 7, 2021

(54) METHOD OF DECOMPOSING BY-PRODUCT IN PHENOL PREPARATION PROCESS

(71) Applicant: LG CHEM, LTD., Seoul (KR)

(72) Inventors: Minsuk Kang, Daejeon (KR); Sang Beom Lee, Daejeon (KR); Sung Ho Lee, Daejeon (KR); Joon Ho Shin, Daejeon (KR); Sangeun Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/624,835

(22) PCT Filed: Aug. 17, 2018

(86) PCT No.: PCT/KR2018/009462
§ 371 (c)(1),
(2) Date: Dec. 19, 2019

(87) PCT Pub. No.: WO2019/098502
PCT Pub. Date: May 23, 2019

(65) Prior Publication Data
US 2020/0122053 A1    Apr. 23, 2020

(30) Foreign Application Priority Data
Nov. 20, 2017  (KR) .................. 10-2017-0154970

(51) Int. Cl.
*B01D 3/00*      (2006.01)
*B01D 3/14*      (2006.01)
(Continued)

(52) U.S. Cl.
CPC ............. *B01D 3/009* (2013.01); *B01D 3/143* (2013.01); *C07C 7/04* (2013.01); *C07C 37/74* (2013.01); *C07C 45/82* (2013.01)

(58) Field of Classification Search
CPC ........... C07C 1/20; C07C 37/52; C07C 37/74; C07C 45/82; C07C 15/085; C07C 15/44;
(Continued)

(56) References Cited

U.S. PATENT DOCUMENTS 3,180,897 A  *  4/1965  Sodomann .............. C07C 37/86
                                                       568/754
3,850,996 A       11/1974  Nixon
(Continued)

FOREIGN PATENT DOCUMENTS

DE        1 105 878 B        5/1961
DE         1105878 B  *      5/1961  ............. C07C 37/86
(Continued)

OTHER PUBLICATIONS

Zou et al., Recycling of valuable chemicals through the catalytic decomposition of phenol tar in cumene process. Process Safety and Environmental Protection, vol. 91, Issue 5, pp. 391-396 (2013).

*Primary Examiner* — Latosha Hines
(74) *Attorney, Agent, or Firm* — Dentons US LLP

(57) ABSTRACT

A method of decomposing a phenol by-product produced in a phenol preparation process, in which acetophenone separated from a distillation column is mixed with tar separated and collected in a decomposition reactor, thereby significantly decreasing viscosity of tar. The decomposition method according to the present invention allows tar to have sufficient viscosity for flowability even at room temperature, whereby transfer and storage of tar may be more smoothly done without using any heating device for transfer of tar.

12 Claims, 3 Drawing Sheets

(51) Int. Cl.
*C07C 7/04* (2006.01)
*C07C 37/74* (2006.01)
*C07C 45/82* (2006.01)

(58) Field of Classification Search
CPC .......... C07C 39/04; C07C 49/78; C07C 7/04; B01D 3/009; B01D 3/143; Y02P 20/10
See application file for complete search history.

(56) References Cited

U.S. PATENT DOCUMENTS

| | | | |
|---|---|---|---|
| 4,246,203 A | 1/1981 | Wirth | |
| 5,457,244 A | 10/1995 | Dyckman et al. | |
| 5,504,251 A | * 4/1996 | Dyckman | ............... C07C 7/148 |
| | | | 568/754 |
| 6,965,056 B1 | 11/2005 | Taggart, II et al. | |

FOREIGN PATENT DOCUMENTS

| | | |
|---|---|---|
| EP | 0 168 358 A1 | 1/1986 |
| JP | 52-35656 A | 3/1977 |
| JP | 8-310978 A | 11/1996 |
| JP | 2011-500831 A | 1/2011 |
| KR | 0161038 B1 | 8/1998 |
| KR | 10-0262026 B1 | 4/2000 |
| KR | 2001-0103198 A | 11/2001 |
| KR | 10-0665764 B1 | 12/2006 |
| KR | 10-2010-0132963 A | 12/2010 |

* cited by examiner

[FIG. 1]
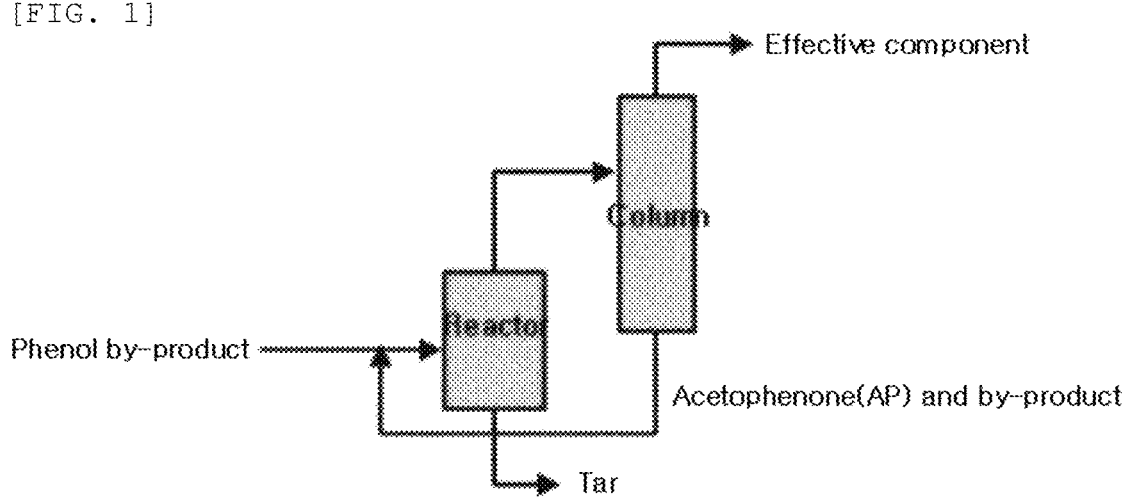
[FIG. 2]
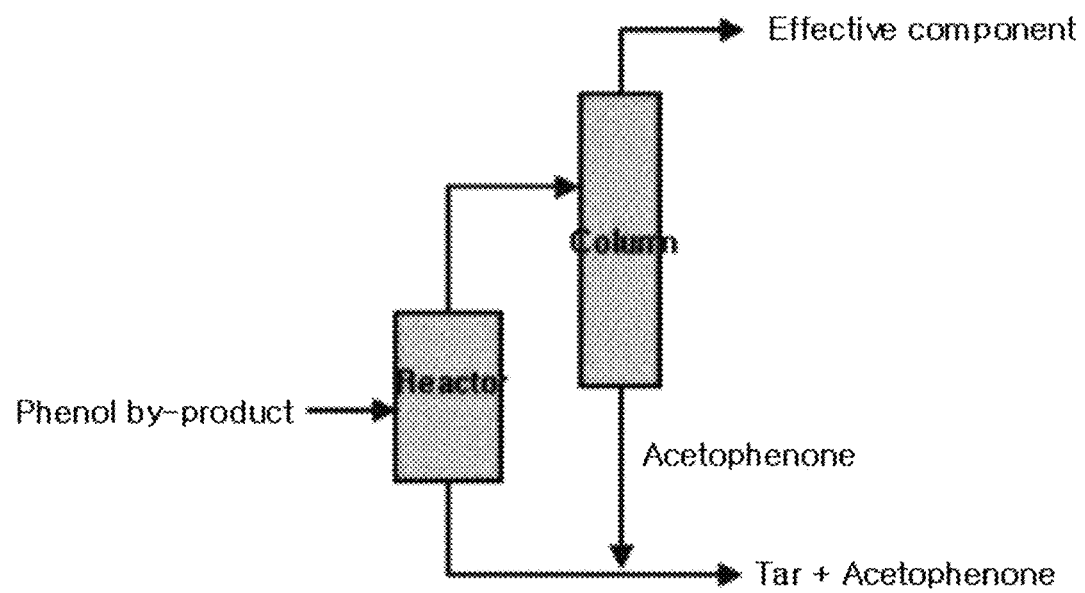

[FIG. 3]
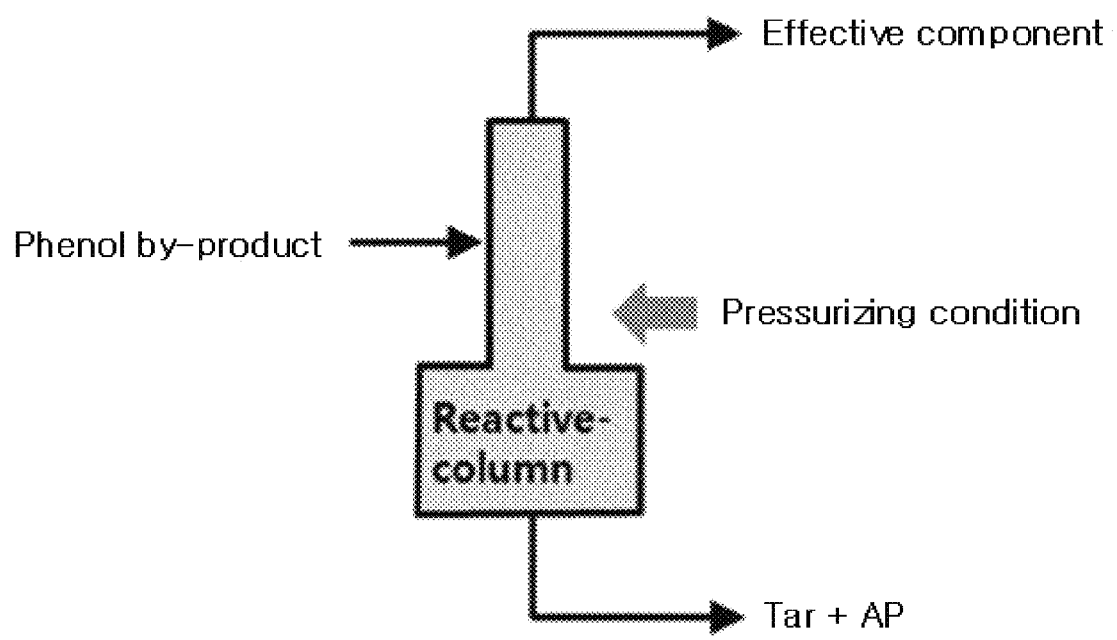
[FIG. 4]
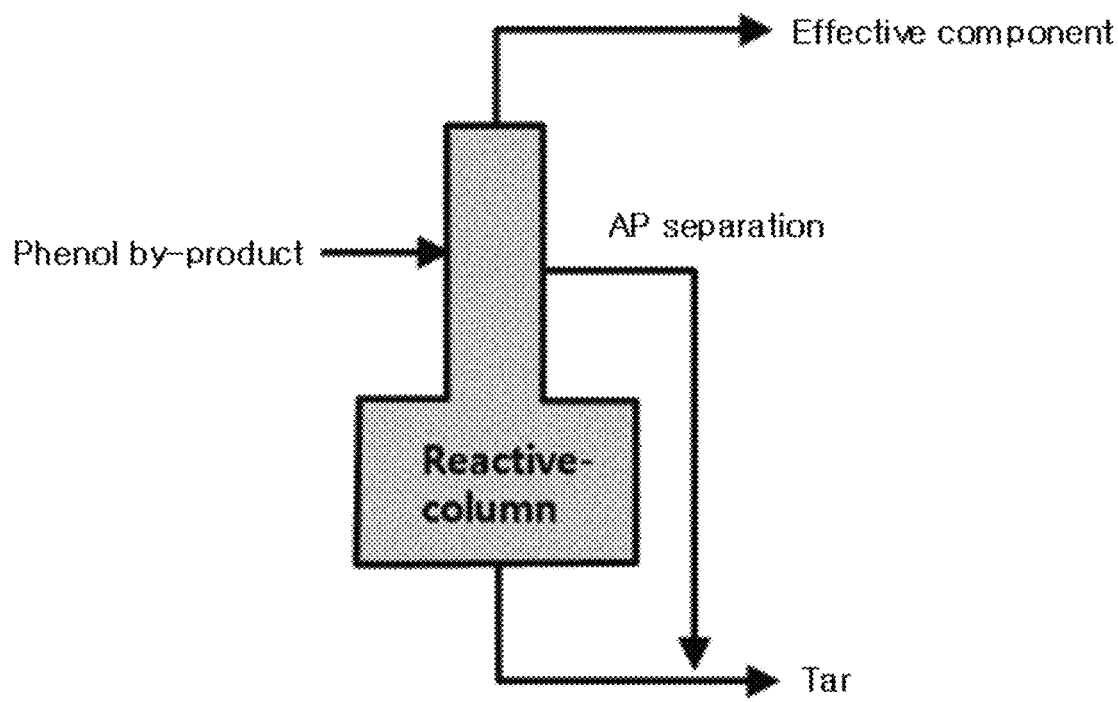

[FIG. 5]
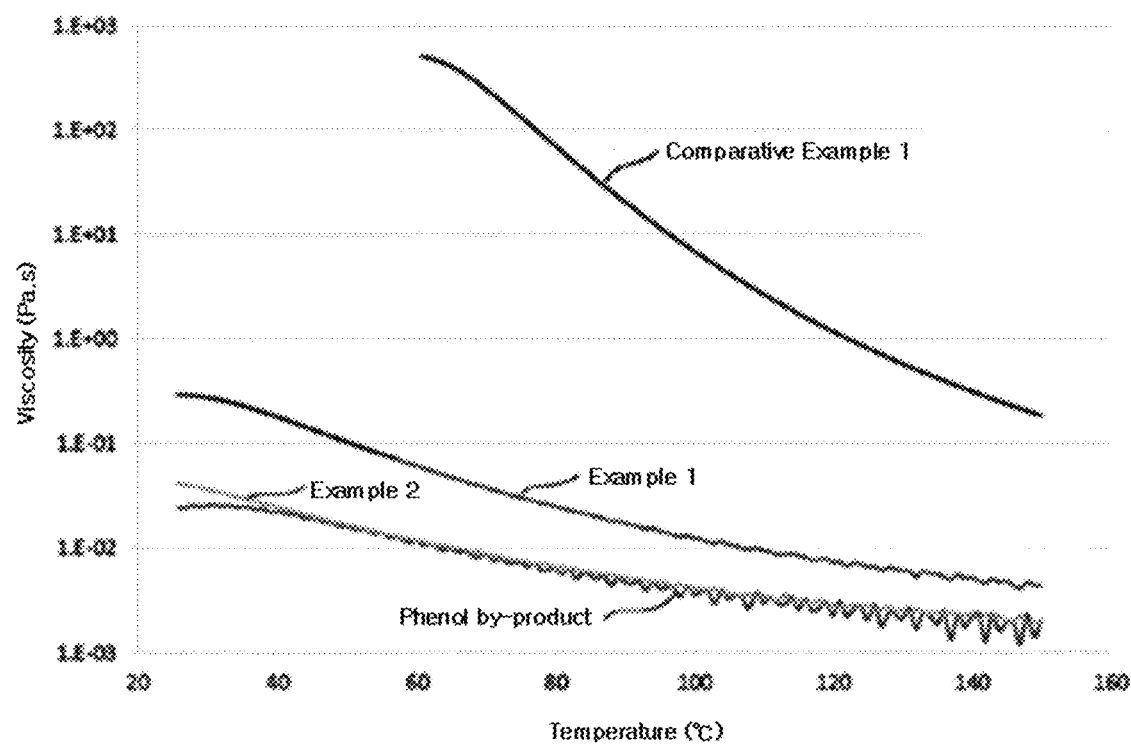

METHOD OF DECOMPOSING BY-PRODUCT IN PHENOL PREPARATION PROCESS

CROSS-REFERENCE TO RELATED APPLICATIONS

This application is the U.S. national phase of international Application No. PCT/KR2018/009462, filed on Aug. 17, 2018, and claims the benefit of priority to Korean Patent Application No. 10-2017-0154970, filed on Nov. 20, 2017, the disclosure of which in their entirety is incorporated herein as a part of the specification.

TECHNICAL FIELD

The present invention relates to a method of decomposing a by-product produced in a phenol preparation process, and more particularly, to a method of improving transfer and storability of tar separated from the by-product.

BACKGROUND ART

About 95% of phenols used around the world are generally produced by a three-step Hock process. The three-step Hock process includes (1) a step of alkylating benzene by propylene to form cumene, (2) a step of oxidizing cumene to cumene hydroperoxide (CHP) by binding the cumene with oxygen, and (3) a step of decomposing CHP into phenol and acetone in the presence of a sulfuric acid catalyst. In the step of cumene oxidation, by-products such as acetophenone (AP), dimethylbenzyl alcohol (DMBA), dicumylperoxide (DCP), and dicumyl (DC) are produced, and in the step of CHP decomposition, by-products such as hydroxyacetone (HA), 2-methylbenzofuran (2MBF), α-methylstyrene (AMS), mesityl oxide (MO), α-methylstyrene dimer (AMS dimer), and cumyl phenol (CP) are produced.

In a stream in which phenol, acetone, and various by-products produced by the above process are mixed, unreacted cumene, acetone, AMS, HA, and the like are separated as overhead products, and phenol and some AMS, 2MBF, other impurities, and the like are separated as bottom products. A phenol compound separated as a bottom product is added to a phenol column, and impurities such as DCP, CP, AMS dimers, or tar are separated as a bottom product and removed.

There are many studies in progress to increase the yield and purity of useful products contained in impurities in a step of collecting tar in the impurities.

DISCLOSURE

Technical Summary

An object of the present invention is to provide a method which may decrease viscosity of tar in by-products produced in a phenol preparation process.

Another object of the present invention is to provide a decomposition device which may effectively decompose the by-product from the phenol preparation process.

In one general aspect, a method of decomposing a phenol by-product, includes:

supplying a phenol by-product produced in a phenol and acetone preparation process to a decomposition reactor to perform a decomposition reaction;

collecting tar by the decomposition reaction;

separating an effective component and acetophenone from a decomposition reaction product, respectively; and mixing the separated acetophenone with the tar to form a tar-acetophenone mixed stream.

According to an exemplary embodiment, the method may include:

collecting the tar from a lower portion of the decomposition reactor by the decomposition reaction;

collecting an upper fraction containing an effective component and acetophenone from an upper portion of the decomposition reactor;

sending the upper fraction to a distillation column to separate the effective component and acetophenone; and mixing the separated acetophenone with the tar to collect the tar-acetophenone mixed stream.

According to an exemplary embodiment, the decomposition reactor may be a reaction distillation column of a type in which a reactor and a distillation column are integrated, and the method may include:

collecting tar from a lower portion of the reaction distillation column;

collecting acetophenone from a middle portion of the reaction distillation column;

collecting an effective component from an upper portion of the reaction distillation column; and mixing the separated and collected acetophenone with the tar to collect a tar-acetophenone mixed stream.

The decomposition reactor may be a reaction distillation column of a type in which a reactor and a distillation column are integrated, and the method may include:

collecting tar and acetophenone from a lower portion of the reaction distillation column;

subjecting an inside of the reaction distillation column to a pressurizing condition to collect acetophenone from a lower portion of the reactor;

collecting an effective component from an upper portion of the reaction distillation column; and collecting a tar-acetophenone mixed stream from a lower portion of the reaction distillation column.

According to an exemplary embodiment, the tar-acetophenone mixed stream may be transferred at 25° C. or higher.

According to an exemplary embodiment, the tar-acetophenone mixed stream may have a viscosity of 60 Pa·s or less at 80° C.

According to an exemplary embodiment, a mixing ratio of the tar and the acetophenone may be 1:0.1 to 1:1.

According to an exemplary embodiment, the acetophenone separated from the distillation column may be collected from a lower portion of the distillation column.

According to an exemplary embodiment, the effective component collected by the decomposition method may include phenol, α-methylstyrene, and cumene.

In another general aspect, a phenol by-product decomposition device includes:

a decomposition reactor for decomposing a phenol by-product produced in a phenol and acetone preparation process;

a tar transfer tube for transferring tar collected from a lower portion of the decomposition reactor to a tar storage device;

an effective component collection unit for collecting an effective component including phenol, AMS, and cumene components from the phenol by-product; and an acetophenone collection unit for collecting acetophenone from the phenol by-product, wherein the tar transfer tube and the acetophenone collection unit are connected to each other.

According to an exemplary embodiment, the phenol by-product decomposition device may include:

an upper fraction collection unit for collecting an upper fraction containing an effective component and acetophenone, which is provided in an upper portion of the decomposition reactor;

a distillation column for separating acetophenone and the effective component from the upper fraction, which is connected to the upper fraction collection unit;

an effective component collection unit which is provided in an upper portion of the distillation column; and an acetophenone collection unit which is provided in a lower portion of the distillation column and connected to the tar transfer tube for tar collected from the tar collection unit.

According to an exemplary embodiment, the decomposition reactor may be a reaction distillation column of a type in which a reactor and a distillation column are integrated, and the phenol by-product decomposition device may include:

a tar collection unit provided in a lower portion of the reaction distillation column;

a tar transfer line for transferring the tar collected from the tar collection unit;

an acetophenone collection unit provided in a lower portion of the reaction distillation column;

an acetophenone transfer line connected to the tar transfer line for mixing the acetophenone collected from the acetophenone collection unit with the collected tar; and an effective component collection unit which is provided in an upper portion of the reaction distillation column, wherein an inside of the reaction distillation column is subjected to a pressurizing condition.

According to an exemplary embodiment, the decomposition reactor may be a reaction distillation column of a type in which a reactor and a distillation column are integrated, and the phenol by-product decomposition device may include:

a tar collection unit provided in a lower portion of the reaction distillation column;

a tar transfer line for transferring the tar collected from the tar collection unit;

an acetophenone collection unit provided in a middle portion of a side of the reaction distillation column;

an acetophenone transfer line connected to the tar transfer line for mixing the acetophenone collected from the acetophenone collection unit with the collected tar; and an effective component collection unit which is provided in an upper portion of the reaction distillation column.

In the present invention, acetophenone separated from a distillation column is mixed with tar, whereby viscosity of tar may be significantly decreased and tar may have sufficient viscosity for flowability even at room temperature, and thus, transfer and storage of tar may be done more smoothly without using any heating device for transfer of tar.

BRIEF DESCRIPTION OF DRAWINGS

FIG. 1 shows a conventional phenol by-product decomposition device.

FIG. 2 shows a phenol by-product decomposition device (reactor-distillation column separated type) according to an exemplary embodiment.

FIGS. 3 and 4 show phenol by-product decomposition devices (reactor-distillation column integrated type) according to an exemplary embodiment.

FIG. 5 is a graph showing a viscosity change depending on a temperature change of tar, a phenol by-product, and a mixture of tar and AP.

DETAILED DESCRIPTION

Since the present invention may be variously modified and have several exemplary embodiments, specific exemplary embodiments will be shown in the accompanying drawings and be described in detail in a detailed description. However, it should be understood that this is not to limit the present invention to a certain embodiment, but is to include all modifications, equivalents, or substitutes included in the spirits and technical scope of the present invention. When it is determined that the detailed description of the known art related to the present invention may obscure the gist of the present invention, the detailed description thereof will be omitted.

A percentage means % by weight unless otherwise stated.

In general, a phenol by-product produced in a phenol and acetone preparation process is decomposed in a decomposition reactor, added to a distillation column to be separated into an effective component (such as α-methylstyrene, phenol or cumene), acetophenone (AP), and tar, and collected. In the decomposition reactor, decomposed tar may be separated and collected to be used as a fuel. Here, since the tar separated from the decomposition reactor has a higher viscosity at a lower temperature, there has been a problem in that smooth transfer and storage were difficult.

In order to solve the conventional problem, the present invention provides a method of decomposing a phenol by-product, the method including:

supplying a phenol by-product produced in a phenol preparation process to a decomposition reactor to perform a decomposition reaction;

collecting tar from a lower portion of the decomposition reactor by the decomposition reaction;

separating and collecting an effective component and acetophenone from a decomposition reaction product, respectively; and mixing the separated acetophenone with the tar to form a tar-acetophenone mixed stream.

In the present invention, a "phenol by-product" refers to a by-product produced in a phenol preparation process.

In the present invention, the tar may further contain by-products other than the component separated from an effective component collection unit after the reaction, and the effective component collected from the upper portion may contain phenol, AMS, and cumene among the products obtained by decomposition of the phenol by-product.

Conventionally, as shown in FIG. 1, in order to increase a collection rate of the effective component collected from the phenol by-product, a method in which acetophenone and other by-products in addition to the effective component fractionated in a distillation column are resupplied to the phenol by-product supplied to a decomposition reactor, has been used, and acetophenone was finally separated and removed.

In the present invention, acetophenone which was conventionally separated from the distillation column and removed, is mixed with tar separated from the decomposition reactor and transferred, whereby viscosity of the tar may be significantly decreased, as well as the mixed stream may maintain a low viscosity even at room temperature, and thus, transfer and storage of the collected tar may be more smoothly done.

In the conventional phenol by-product separation process, the tar separated from a lower portion of the reactor has a significantly higher viscosity at a lower temperature, thereby having a problem in that smooth transfer and storage were difficult.

In general, viscosity of a fluid which is flowable in the transfer pipe may be about 60 Pa·s at 80° C., and viscosity of tar at room temperature may be about 1000 Pa·s. Accordingly, in order to transfer tar using a transfer pipe used in a general process, it is necessary to lower the viscosity of tar to 60 Pa·s or less. In general, in order to transfer tar, it is necessary to increase temperature or mix tar with a certain material.

In the present invention, using the fact that acetophenone present in the phenol by-product may be mixed with tar to lower viscosity of tar, in order to solve the problem of transfer and storage of tar at room temperature, acetophenone separated from the reactor is mixed with tar to significantly lower the viscosity of tar, thereby making transfer and storage of tar smooth even under a condition of room temperature to decrease energy required for the process.

In addition, since the tar-acetophenone mixture separated and collected as described above is used as a fuel as it is, an additional process of separating acetophenone contained in the tar again is not needed, and thus, efficiency of the process may be increased, as compared with additionally mixing other materials.

The tar-acetophenone mixed stream may have a viscosity of 30 Pa·s or less at 25° C., preferably 20 Pa·s or less, and more preferably 10 Pa·s or less, and depending on a mixing ratio and an operating temperature of tar and acetophenone, the viscosity may be 1 Pa·s or less or 0.5 Pa·s or less, and may be significantly lowered to 0.3 Pa·s or less. Accordingly, in the present invention, tar and acetophenone are mixed and transferred, thereby smoothly transferring tar under a temperature condition of room temperature (at about 25° C.) without raising the temperature. In addition, the viscosity may be decreased by 10 times as the temperature rises.

In addition, the mixing ratio of tar and acetophenone may be optionally selected, may be varied depending on a composition of a phenol composition (an AP content in the existing phenol by-product) or a degree of AP separated from an effective component in the distillation column, and for example, may be 10:1 to 1:10 in a weight ratio, and as the mixing ratio of acetophenone is increased, the viscosity of the mixed stream may be decreased, and in order to represent sufficient flowability at room temperature, it is preferred that the mixing ratio of tar and acetophenone is 1:0.3 or more or 1:0.4 or more and 1:0.9 or less or 1:0.8 or less in a weight ratio.

According to an exemplary embodiment, the decomposition method may include:

collecting tar from a lower portion of a decomposition reactor and collecting an upper fraction containing an effective component and acetophenone from an upper portion of the decomposition reactor;

sending the upper fraction to a distillation column to separate the effective component and the acetophenone; and mixing the separated acetophenone with tar to collect a tar-acetophenone mixed stream.

Otherwise, according to an exemplary embodiment, the decomposition reactor may be a reaction distillation column of a type in which a reactor and a distillation column are integrated, and the decomposition method may include:

collecting tar from a lower portion of the reaction distillation column;

subjecting an inside of the reaction distillation column to a pressurizing condition to raise viscosity of acetophenone to collect acetophenone from a lower portion of the reactor;

collecting an effective component from an upper portion of the reaction distillation column; and mixing the separated acetophenone with the tar to collect a tar-acetophenone mixed stream.

Otherwise, the decomposition reactor may be a reaction distillation column of a type in which a reactor and a distillation column are integrated, and the decomposition method may include:

collecting tar from a lower portion of the reaction distillation column;

collecting acetophenone from a middle portion of the reaction distillation column;

collecting an effective component from an upper portion of the reaction distillation column; and mixing the separated and collected acetophenone with the tar to collect a tar-acetophenone mixed stream.

Herein, the "reaction distillation column" refers to a distillation column of a type in which a reactor and a distiller are integrated.

The effective component collected from the upper portion of the distillation column may contain phenol, α-methylstyrene (AMS), and cumene, the distillation column may further have a collection unit of other by-products for collecting by-products, other than the effective component collection unit and the acetophenone collection unit, and the by-product is supplied to a phenol by-product supply unit which is connected to the decomposition reactor to be resupplied to the decomposition reactor.

In addition, the present invention provides a phenol by-product decomposition device, including:

a decomposition reactor for decomposing a phenol by-product produced in a phenol and acetone preparation process;

a tar collection unit provided in a lower portion of the decomposition reactor;

a tar transfer tube for transferring tar collected from the tar collection unit to a tar storage device;

an effective component collection unit for collecting an effective component containing phenol, AMS, and cumene components contained in the phenol by-product; and an acetophenone collection unit for collecting acetophenone contained in the phenol by-product, wherein the tar transfer tube and the acetophenone collection unit are connected to each other.

For example, the present invention provides a phenol by-product decomposition device which may decompose a phenol by-product from a decomposition device in which a decomposition reactor and a distillation column are connected, as shown in FIG. 2, and more specifically, may include:

a decomposition reactor for decomposing a phenol by-product produced in a phenol and acetone preparation process;

a tar collection unit provided in a lower portion of the decomposition reactor;

a tar transfer tube for transferring tar collected from the tar collection unit to a tar storage device;

an upper fraction collection unit for collecting an upper fraction containing an effective component and acetophenone, which is provided in an upper portion of the decomposition reactor;

a distillation column for separating acetophenone and the effective component from the upper fraction, which is connected to the upper fraction collection unit;

an effective component collection unit which is provided in an upper portion of the distillation column; and an acetophenone collection unit which is provided in a lower portion of the distillation column and connected to the tar transfer tube for tar collected from the tar collection unit.

Otherwise, the decomposition reactor may be a reaction distillation column of a type in which a reactor and a distillation column are integrated as shown in FIG. 3, and the decomposition device may include:

a tar collection unit provided in a lower portion of the reaction distillation column;

a tar transfer line for transferring the tar collected from the tar collection unit;

an acetophenone collection unit provided in a lower portion of the reaction distillation column;

an acetophenone transfer line connected to the tar transfer line for mixing the acetophenone collected from the acetophenone collection unit with the collected tar; and an effective component collection unit which is provided in an upper portion of the reaction distillation column, wherein an inside of the reaction distillation column is subjected to a pressurizing condition.

According to an exemplary embodiment, the acetophenone separated under the pressurizing condition has a higher viscosity and is separated in the lower portion of the reactor, thereby being separated with tar without having an additional separation line.

Otherwise, the decomposition reactor may be the reaction distillation column of a type in which a reactor and a distillation column are integrated as shown in FIG. 4, and the decomposition device may include:

a tar collection unit provided in a lower portion of the reaction distillation column;

a tar transfer line for transferring the tar collected from the tar collection unit;

an acetophenone collection unit provided in a middle portion of a side of the reaction distillation column;

an acetophenone transfer line connected to the tar transfer line for mixing the acetophenone collected from the acetophenone collection unit with the collected tar; and an effective component collection unit which is provided in an upper portion of the reaction distillation column.

In the present invention, acetophenone separated from a distillation column is mixed with tar, whereby viscosity of tar may be significantly decreased and tar may have sufficient viscosity for flowability even at room temperature, and thus, transfer and storage of tar may be more smoothly done without using any heating device for transfer of tar.

EXAMPLES

Hereinafter, the Examples of the present invention will be described in detail so as to be easily practiced by a person with ordinary skill in the art to which the present invention pertains. However, the present invention may be implemented in various different forms and is not limited to the Examples described herein.

Components of a phenol by-product produced in a phenol and acetone preparation process are listed in the following Table 1, and viscosities of the phenol by-product, and tar and a tar-acetophenone mixture which were collected from the phenol by-product are listed in Table 2 and FIG. 5.

TABLE 1

<Unit, kg/hr>

| Component | Phenol by-product (% by weight) | Collected tar (% by weight) |
|---|---|---|
| Phenol | 42.1 | 1.5 |
| Alpha-methylstyrene | 78.8 | 1.7 |
| Acetophenone | 192.2 | 1.2 |
| Cumyl phenol | 280.4 | 19.5 |
| Dimers of alpha-methylstyrene | 154.0 | 3.3 |
| Others | 252.5 | 204.2 |
| Total | 1000.0 | 231.5 |

TABLE 2

| Classification | | Ref Phenol by-product = 1 | Comparative Example 1 Tar = 1 | Example 1 Tar:Acetophenone = 1:0.5 | Example 2 Tar:Acetophenone = 1:1 |
|---|---|---|---|---|---|
| Viscosity (Pa · s) | 25° C. | 0.024 | 512.799 | 0.295 | 0.042 |
| | 80° C. | 0.005 | 62.441 | 0.024 | 0.006 |
| | 150° C. | 0.002 | 0.188 | 0.004 | 0.002 |

As shown in Table 2 above, it is recognized that tar which was not mixed (Comparative Example 1) had no flowability at room temperature and its viscosity was gradually decreased at a temperature of 80° C. or higher; however, a tar-acetophenone mixed stream of Examples 1 and represented significantly low viscosity even at room temperature as compared with the viscosity of tar at 80° C. or higher, and a mixed stream of Example 2 had a very similar viscosity to the viscosity of the phenol by-product even at room temperature, thereby representing sufficient flowability even at room temperature.

The present invention has been described in detail in specific parts, and it is obvious that such specific technique is only a preferred embodiment to a person skilled in the art and the scope of the present invention is not limited thereby. Thus, the substantial scope of the present invention will be defined by the appended claims and their equivalents.

The invention claimed is:

1. A method of decomposing a phenol by-product, the method comprising:
supplying the phenol by-product produced in a phenol and acetone preparation process to a decomposition reactor to perform a decomposition reaction to produce tar and a decomposition reaction product, wherein the decomposition reactor is a reaction distillation column of a type in which the reactor and the distillation column are integrated;

collecting the tar produced by the decomposition reaction via a tar transfer tube located at a lower portion of the reaction distillation column;

separating an effective component and acetophenone from the decomposition reaction product;

collecting the acetophenone via an acetophenone collection unit located at a middle portion of the reaction distillation column;

collecting the effective component via an effective component collection unit located at an upper portion of the reaction distillation column;

mixing the acetophenone collected via the acetophenone collection unit with the tar collected via the tar transfer tube to form a tar-acetophenone mixed stream; and collecting the tar-acetophenone mixed stream.

2. A method of decomposing a phenol by-product, the method comprising:

supplying the phenol by-product produced in a phenol and acetone preparation process to a decomposition reactor to perform a decomposition reaction to produce tar and a decomposition reaction product;

collecting the tar from a lower portion of the decomposition reactor via a tar transfer tube;

separating an effective component and acetophenone from the decomposition reaction product;

collecting an upper fraction containing the effective component and the acetophenone via an upper fraction collection unit located at an upper portion of the decomposition reactor;

sending the upper fraction to a distillation column to separate the effective component and the acetophenone;

collecting the separated effective component from the distillation column via an effective component collection unit located at an upper portion of the distillation column;

collecting the separated acetophenone from the distillation column via an acetophenone collection unit located at a lower portion of the distillation column; and mixing the separated acetophenone collected from the distillation column with the tar collected from the decomposition reactor to form a tar-acetophenone mixed stream, and collecting the tar-acetophenone mixed stream.

3. The method of decomposing a phenol by-product of claim 1, wherein the tar-acetophenone mixed stream is transferred at a temperature of 25° C. or higher.

4. The method of decomposing a phenol by-product of claim 1, wherein the tar-acetophenone mixed stream has a viscosity of 60 Pa·s or less at 80° C.

5. The method of decomposing a phenol by-product of claim 1, wherein a mixing ratio of the tar and the acetophenone is 10:1 to 1:10.

6. The method of decomposing a phenol by-product of claim 1, wherein the effective component includes phenol, α-methylstyrene, and cumene.

7. The method of decomposing a phenol by-product of claim 2, wherein the tar-acetophenone mixed stream is transferred at a temperature of 25° C. or higher.

8. The method of decomposing a phenol by-product of claim 2, wherein the tar-acetophenone mixed stream has a viscosity of 60 Pa·s or less at 80° C.

9. The method of decomposing a phenol by-product of claim 2, wherein a mixing ratio of the tar and the acetophenone is 10:1 to 1:10.

10. The method of decomposing a phenol by-product of claim 2, wherein the effective component includes phenol, α-methylstyrene, and cumene.

11. The method of decomposing a phenol by-product of claim 1, wherein the tar transfer tube and the acetophenone collection unit are connected to each other.

12. The method of decomposing a phenol by-product of claim 2, wherein the tar transfer tube and the acetophenone collection unit are connected to each other.

* * * * *